US008231929B2

(12) United States Patent
Sun

(10) Patent No.: US 8,231,929 B2
(45) Date of Patent: Jul. 31, 2012

(54) MEDICAL DEVICE COATING PROCESS

(75) Inventor: Jichao Sun, West Lafayette, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 1082 days.

(21) Appl. No.: 11/877,369

(22) Filed: Oct. 23, 2007

(65) Prior Publication Data

US 2008/0175980 A1 Jul. 24, 2008

Related U.S. Application Data

(60) Provisional application No. 60/857,908, filed on Nov. 9, 2006.

(51) Int. Cl.
*A61L 33/00* (2006.01)

(52) U.S. Cl. ..... 427/2.24; 401/208; 623/1.46; 623/1.49; 427/2.25; 424/9.45; 424/426; 424/422; 424/423; 424/424; 424/425; 424/484; 424/486; 424/487; 424/488; 118/420; 118/303; 118/410

(58) Field of Classification Search .................. 424/422, 424/9.45, 426; 623/1.46, 1.49; 401/208; 118/420

See application file for complete search history.

(56) References Cited

U.S. PATENT DOCUMENTS

| | | | | |
|---|---|---|---|---|
| 4,731,073 | A | 3/1988 | Robinson | |
| 5,922,393 | A | 7/1999 | Jayaraman | |
| 6,156,064 | A | 12/2000 | Chouinard | |
| 6,641,831 | B1 * | 11/2003 | Schierholz | 424/422 |
| 6,752,826 | B2 | 6/2004 | Holloway | |
| 6,821,295 | B1 | 11/2004 | Farrar | |
| 6,860,946 | B2 | 3/2005 | Hossainy et al. | |
| 6,939,377 | B2 | 9/2005 | Jayaraman et al. | |
| 7,112,298 | B2 | 9/2006 | Kampa et al. | |
| 7,232,490 | B1 | 6/2007 | Hossainy | |
| 2002/0065552 | A1 * | 5/2002 | Jayaraman et al. | 623/1.46 |
| 2003/0149471 | A1 | 8/2003 | Briana et al. | |
| 2003/0215564 | A1 | 11/2003 | Heller et al. | |
| 2004/0062592 | A1 * | 4/2004 | Shekalim et al. | 401/208 |
| 2004/0243100 | A9 | 12/2004 | Kampa et al. | |
| 2005/0074544 | A1 | 4/2005 | Pacetti et al. | |
| 2005/0147734 | A1 | 7/2005 | Seppala et al. | |
| 2005/0196518 | A1 | 9/2005 | Stenzel | |
| 2005/0233061 | A1 | 10/2005 | Schwarz | |
| 2006/0030936 | A1 | 2/2006 | Weber | |

OTHER PUBLICATIONS

International Search Report for PCT/US2007/023471; Dated Dec. 17, 2008.

* cited by examiner

*Primary Examiner* — Dah-Wei Yuan
*Assistant Examiner* — Andrew Bowman
(74) *Attorney, Agent, or Firm* — Brinks Hofer Gilson & Lione

(57) ABSTRACT

Methods for coating medical devices for implantation within a body vessel are provided comprising providing a cylindrical container, placing a medical device inside the cylindrical container, and applying a polymer in liquid form inside the container.

20 Claims, 2 Drawing Sheets

MEDICAL DEVICE COATING PROCESS

RELATED APPLICATIONS

The present patent document claims the benefit of the filing date under 35 U.S.C. §119(e) of Provisional U.S. Patent Application Ser. No. 60/857,908, filed Nov. 9, 2006, which is hereby incorporated by reference.

TECHNICAL FIELD

This invention relates generally to human and veterinary medical devices, and more particularly to methods of coating devices.

BACKGROUND

Various implantable medical devices are advantageously inserted within various body vessels, for example to improve blood flow through a restricted or weakened vessel. Minimally invasive techniques and instruments for placement of intraluminal medical devices have been developed to treat and repair undesirable conditions within body vessels. Various percutaneous methods of implanting medical devices within the body using intraluminal transcatheter delivery systems can be used to treat a variety of conditions. One or more intraluminal medical devices can be introduced to a point of treatment within a body vessel using a delivery catheter device passed through the vasculature communicating between a remote introductory location and the implantation site, and released from the delivery catheter device at the point of treatment within the body vessel. Intraluminal medical devices can be deployed in a body vessel at a point of treatment and the delivery device subsequently withdrawn from the vessel, while the medical device retained within the vessel to provide sustained improvement in blood flow or to increase vessel patency.

Implantable medical devices are effective for minimally invasive treatment of vascular occlusions such as atherosclerosis and restenosis and treatment of weakened or diseased vessels. Such implantable medical devices reestablish a flow lumen, reinforces the weakened vessel, and prevents occlusion or stenosis.

Coatings are often applied to the implantable medical device to improve the biocompatibility of the device and minimize or prevent occlusion of the device. Methods of coating the abluminal surface of a tubular medical device are known. U.S. published patent application No. 2005/0233061 A1 describes a method and apparatus for coating a medical device using a coating head. In one embodiment a slide coating is applied to the abluminal surface of a medical device. U.S. published patent application No. 2005/0196518 A1 describes a method of coating a medical device by substantially simultaneously applying a coating composition and partially drying the coating composition. U.S. published patent publication No. 2005/0147734 A1 describes a method for application of therapeutic and protect coatings to the abluminal tubular medical devices by placing the medical device on a core and passing it through an extrusion coating machine.

Inhibiting or preventing thrombosis and platelet deposition on an implantable device within the body is important in promoting continued function of the medical device within the body, particularly within blood vessels. Post-implantation thrombosis and platelet deposition on surfaces of implantable medical devices prosthesis undesirably reduce the patency rate of many implantable medical devices. For example, thrombosis and platelet deposition within an endovascular prosthesis may occlude the conduit defined by the endovascular prosthesis or compromise the function of an implanted valve by limiting the motion or responsiveness of moveable portions of the device such as valve leaflets. Many factors contribute to thrombosis and platelet deposition on the surfaces of implanted prosthesis. The properties of the material or materials forming the endovascular prosthesis are believed to be one important factor that can contribute to the likelihood of undesirable levels of post-implantation thrombus formation or platelet deposition on the implanted device. The formation of blood clots, or thrombus, on the surface of an endovascular prosthesis can both degrade the intended performance of the prosthesis and even undesirably restrict or occlude desirable fluid flow within a body vessel. Coatings may be used to prevent occlusion of the implantable medical device. A non-thrombogenic coating may be used to minimize thrombosis on the blood contact surface of the device.

Non-thrombogenic coatings are preferably applied to the luminal surface of the medical device. U.S. Pat. No. 7,112,298 describes a method of forming a medical device comprising applying a polymer coating to a mandrel and constructing the remainder of the medical device around the polymer coated mandrel. What is needed are improved methods for coating medical devices on the luminal and/or abluminal surface. Methods for coating luminal surfaces are useful forming a non-thromobogenic blood contact surface on the medical device.

BRIEF SUMMARY

One embodiment of the present invention provides a method of applying a coating to a luminal surface of an implantable medical device. The method comprises providing the implantable medical device defining a lumen and having a longitudinal axis; rotating the medical device about the longitudinal axis; applying a first polymer in liquid form to the luminal surface; and at least partially solidifying the first polymer while rotating. In some aspects, the method further comprises any of the steps of applying a first bioactive material between luminal surface of the medical device and the first polymer; or admixing the first bioactive material with the first polymer in liquid form; or applying a first bioactive material to an inner surface defined by the first polymer. In some aspects the polymer comprises a polyurethane urea optionally blended with a siloxane containing surface modifying additive.

In another embodiment of the present invention, a method of applying a coating to an abluminal surface of an implantable medical device. The method comprises providing a cylindrical container having a longitudinal axis; placing the medical device defining a lumen inside a cylindrical container; placing a first polymer in liquid form between an inner surface of the cylindrical container and the abluminal surface of the medical device; rotating the cylindrical container about the longitudinal axis; and at least partially solidifying the first polymer while rotating. In some aspects, the method further comprises any of the steps of applying a first bioactive material between luminal surface of the medical device and the first polymer; or admixing the first bioactive material with the first polymer in liquid form; or applying a first bioactive material to an inner surface defined by the first polymer. In some aspects the polymer comprises a polyurethane urea optionally blended with a siloxane containing surface modifying additive. In other aspects, the method further comprises applying a second polymer in liquid form to a luminal surface of the medical device; and at least partially solidifying the second polymer while rotating.

DETAILED DESCRIPTION OF THE DRAWINGS AND THE PRESENTLY PREFERRED EMBODIMENTS

Definitions

Figure 1:
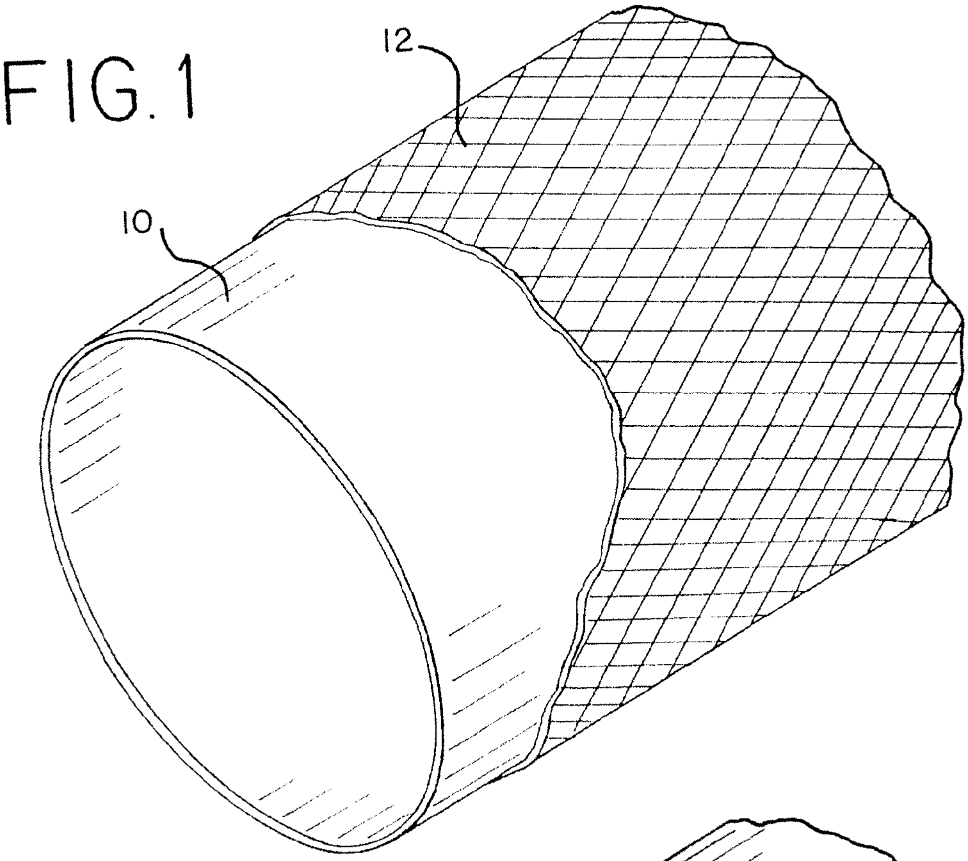
FIG. 1 is a perspective view of an implantable medical device with a coating on luminal surface.

Unless otherwise defined, all technical and scientific terms used herein have the same meaning as commonly understood by one of ordinary skill in the art to which this invention pertains. In case of conflict, the present document, including definitions, will control. Preferred methods and materials are described below, although methods and materials similar or equivalent to those described herein can be used in the practice or testing of the present invention. All publications, patent applications, patents and other references mentioned herein are incorporated by reference in their entirety. The materials, methods, and examples disclosed herein are illustrative only and not intended to be limiting.

The term "polymer" as used herein, refers to a compound derived from monomer subunits which are connected by covalent chemical bonds. A polymer is made up a linked series of repeated monomers. The monomers may be identical, similar or different. The term polymer includes copolymers, for example polymers derived from two types of monomer units, and terpolymers, polymers derived from more than two types of monomer units.

The term "polymer in liquid form" as used herein, refers to liquid form of a polymer or a polymer precursor which is may be neat or a composition. An example of a polymer precursor is monomer subunits. The polymer in liquid form may be a polymer melt. The polymer in liquid form may be a polymer or polymer precursor dissolved, partially dissolved, dispersed or suspended in a media including for example, a solvent. A polymer solution may comprise monomer units, either identical, similar or different, which can polymerize to form a polymer. The polymerization may be affected by removal of the media, heat, sonication, or other polymerization techniques known to one skilled in the art.

The term "lumen" as used herein, refers to an inner surface of a tube or cylinder.

The term "ablumen" as used herein, refers to an outer surface of a tube or cylinder.

The term "implantable" refers to an ability of a medical device to be positioned at a location within a body, such as within a body vessel. Furthermore, the terms "implantation" and "implanted" refer to the positioning of a medical device at a location within a body, such as within a body vessel.

As used herein, "endoluminally," "intraluminally" or "transluminal" all refer synonymously to implantation placement by procedures wherein the prosthesis is advanced within and through the lumen of a body vessel from a remote location to a target site within the body vessel. In vascular procedures, a medical device will typically be introduced "endovascularly" using a catheter over a guidewire under fluoroscopic guidance. The catheters and guidewires may be introduced through conventional access sites to the vascular system, such as through the femoral artery, or brachial and subclavian arteries, for access to the coronary arteries.

As used herein, the term "body vessel" means any body passage lumen that conducts fluid, including but not limited to blood vessels, esophageal, intestinal, billiary, urethral and ureteral passages.

The terms "frame" and "support frame" are used interchangeably herein to refer to a structure that can be implanted, or adapted for implantation, within the lumen of a body vessel.

An "alloy" is a substance composed of two or more metals or of a metal and a nonmetal united, such as by chemical or physical interaction. Alloys can be formed by various methods, including being fused together and dissolving in each other when molten, although molten processing is not a requirement for a material to be within the scope of the term "alloy." As understood in the art, an alloy will typically have physical or chemical properties that are different from its components.

A "biodegradable" material is a material that dissipates upon implantation within a body, independent of the mechanisms by which dissipation can occur, such as dissolution, degradation, absorption and excretion. The actual choice of which type of materials to use may readily be made by one of ordinary skill in the art. Such materials are often referred to by different terms in the art, such as "bioresorbable," "bioabsorbable," or "biodegradable," depending upon the mechanism by which the material dissipates. The prefix "bio" indicates that the erosion occurs under physiological conditions, as opposed to other erosion processes, caused for example, by high temperature, strong acids or bases, UV light or weather conditions.

A "biocompatible" material is a material that is compatible with living tissue or a living system by not being toxic or injurious and not causing immunological rejection.

A "non-bioabsorbable" or "biostable" material refers to a material, such as a polymer or copolymer, which remains in the body without substantial bioabsorption.

A "remodelable material" is a material that, when implanted in vivo, is capable of being resorbed by the body or providing a matrix for the regrowth of autologous cells. In some embodiments, fluid contacting autologous cells on an implanted remodelable material interface can affect the growth of autologous tissue on the implanted remodelable material.

The phrase "controlled release" refers to the release of an agent at a predetermined rate. A controlled release may be constant or vary with time. A controlled release may be characterized by a drug elution profile, which shows the measured rate that the agent is removed from a device in a given solvent environment as a function of time. For example, a controlled release elution profile from a medical device may include an initial burst release associated with the deployment of the medical device followed by a more gradual subsequent release. A controlled release may be a gradient release in which the concentration of the agent released varies over time or a steady state release in which the agent is released in equal amounts over a certain period of time (with or without an initial burst release).

As used herein, the phrase "bioactive agent" refers to any pharmaceutically active agent that produces an intended therapeutic effect on the body to treat or prevent conditions or diseases.

Implantable Medical Device

For the purposes of promoting an understanding of the principles of the invention, reference will now be made to the embodiments illustrated in the drawings and specific language will be used to describe the same. It will nevertheless be understood that no limitation of the scope of the invention is thereby intended, and alterations and modifications in the illustrated device, and further applications of the principles of the invention as illustrated therein are herein contemplated as would normally occur to one skilled in the art to which the invention relates.

Figure 2:
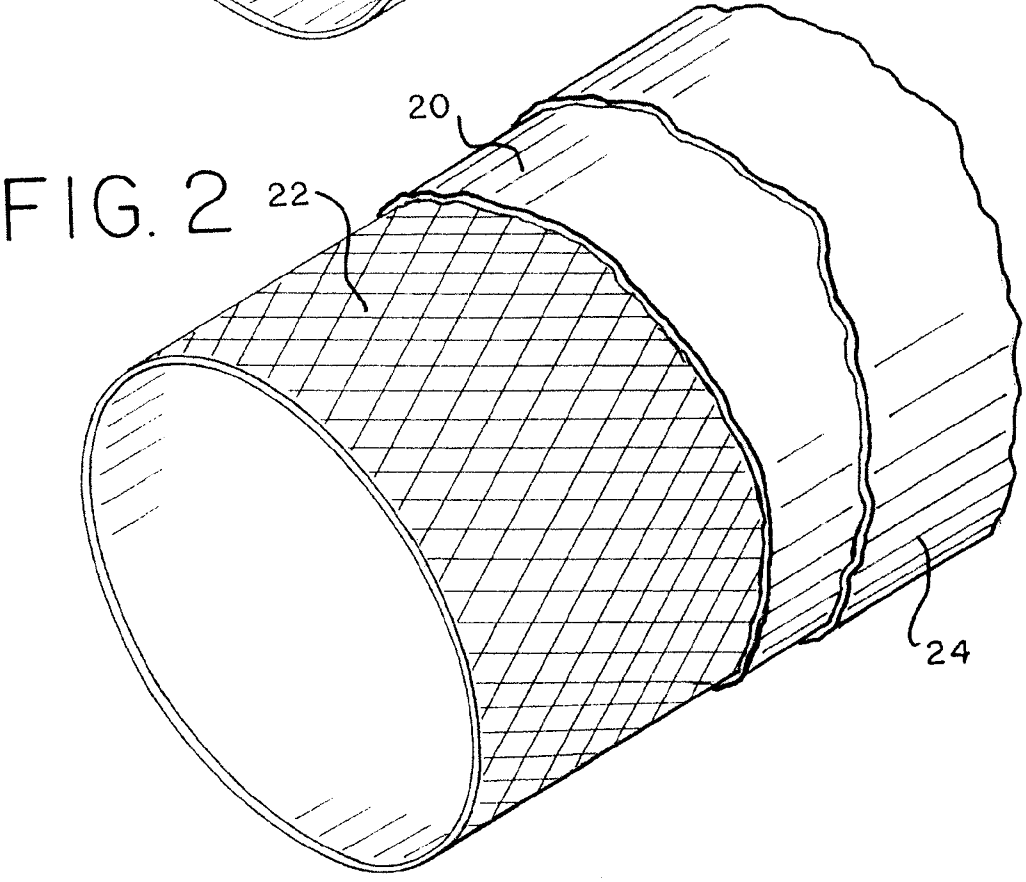
FIG. 2 is a perspective view of an implantable medical device with a coating disposed between an inner surface of a cylindrical container and the abluminal surface of the medical device.

Methods of the present invention comprise coating an implantable medical device. The illustrative medical device 12 in FIG. 1, is coated on at least a portion of the luminal surface with a polymer coating 10. The polymer coating is preferably nonthrombogenic. Nonthrombogenic coatings may comprise a biocompatible polyurethane, a bioactive agent, or a combination thereof. FIG. 2 illustrates an implantable medical device 22 which is coated on at least a portion of the abluminal surface with a polymer coating 20. The abluminal surface is coated by placing a polymer in liquid form between an inner surface of the cylindrical container 24 and the abluminal surface of the medical device. In other embodiments of the present invention, a method of coating the luminal and abluminal surface of the implantable medical device are provided.

Devices of the invention are desirably adapted for deployment within a body lumen. One aspect of the present invention provides a self-expanding or otherwise expandable stent or stent graft for deployment within a bodily passageway, such as a vessel or duct of a patient. The prosthesis is typically delivered and implanted using well-known transcatheter techniques for self-expanding or otherwise expandable prostheses. The medical device, when positioned in a body vessel, may generally conform to the shape of the vessel wall and define a lumen within the vessel or may support the vessel wall, defining a lumen within the vessel.

Polymer Coating

The implantable medical device comprises one or more polymer coatings. Preferably, the polymer coating is thromboresistant. In one embodiment the thromboresistant polymer coating is a biocompatible polyurethane material comprising a surface modifying agent, as described herein.

The thromboresistant material, as disclosed herein, can be selected from a variety of materials, but preferably comprises a biocompatible polyurethane material. One particularly preferred biocompatible polyurethane is THORALON (THORATEC, Pleasanton, Calif.), described in U.S. Pat. Nos. 6,939,377 and 4,675,361, both of which are incorporated herein by reference. The biocompatible polyurethane material sold under the tradename THORALON is a polyurethane base polymer (referred to as BPS-215) blended with a siloxane containing surface modifying additive (referred to as SMA-300). The concentration of the surface modifying additive may be in the range of 0.5% to 5% by weight of the base polymer.

THORALON has been used in certain vascular applications and is characterized by thromboresistance, high tensile strength, low water absorption, low critical surface tension, and good flex life. THORALON is believed to be biostable and to be useful in vivo in long term blood contacting applications requiring biostability and leak resistance. Because of its flexibility, THORALON is useful in larger vessels, such as the abdominal aorta, where elasticity and compliance is beneficial.

The SMA-300 component (THORATEC) is a polyurethane comprising polydimethylsiloxane as a soft segment and the reaction product of diphenylmethane diisocyanate (MDI) and 1,4-butanediol as a hard segment. A process for synthesizing SMA-300 is described, for example, in U.S. Pat. Nos. 4,861,830 and 4,675,361, which are incorporated herein by reference.

The BPS-215 component (THORATEC) is a segmented polyetherurethane urea containing a soft segment and a hard segment. The soft segment is made of polytetramethylene oxide (PTMO), and the hard segment is made from the reaction of 4,4'-diphenylmethane diisocyanate (MDI) and ethylene diamine (ED).

THORALON can be formed as non-porous material or as a porous material with varying degrees and sizes of pores, as described below. Porous THORALON can be formed by mixing the polyetherurethane urea (BPS-215), the surface modifying additive (SMA-300) and a particulate substance in a solvent. The particulate may be any of a variety of different particulates or pore forming agents, including inorganic salts. Preferably the particulate is insoluble in the solvent. The solvent may include dimethyl formamide (DMF), tetrahydrofuran (THF), dimethylacetamide (DMAC), dimethyl sulfoxide (DMSO), or mixtures thereof. The composition can contain from about 5 wt % to about 40 wt % polymer, and different levels of polymer within the range can be used to fine tune the viscosity needed for a given process. The composition can contain less than 5 wt % polymer for some spray application embodiments. The particulates can be mixed into the composition. For example, the mixing can be performed with a spinning blade mixer for about an hour under ambient pressure and in a temperature range of about 18° C. to about 27° C. The entire composition can be cast as a sheet, or coated onto an article such as a mandrel or a mold. In one example, the composition can be dried to remove the solvent, and then the dried material can be soaked in distilled water to dissolve the particulates and leave pores in the material. In another example, the composition can be coagulated in a bath of distilled water. Since the polymer is insoluble in the water, it will rapidly solidify, trapping some or all of the particulates. The particulates can then dissolve from the polymer, leaving pores in the material. It may be desirable to use warm water for the extraction, for example water at a temperature of about 60° C. The resulting pore diameter can also be substantially equal to the diameter of the salt grains.

The porous polymeric sheet can have a void-to-volume ratio from about 0.40 to about 0.90. Preferably the void-to-volume ratio is from about 0.65 to about 0.80. The resulting void-to-volume ratio can be substantially equal to the ratio of salt volume to the volume of the polymer plus the salt. Void-to-volume ratio is defined as the volume of the pores divided by the total volume of the polymeric layer including the volume of the pores. The void-to-volume ratio can be measured using the protocol described in AAMI (Association for the Advancement of Medical Instrumentation) VP20-1994, Cardiovascular Implants—Vascular Prosthesis section 8.2.1.2, Method for Gravimetric Determination of Porosity. The pores in the polymer can have an average pore diameter from about 1 micron to about 400 microns. Preferably the average pore diameter is from about 1 micron to about 100 microns, and more preferably is from about 1 micron to about 10 microns. The average pore diameter is measured based on images from a scanning electron microscope (SEM). Formation of porous THORALON is described, for example, in U.S. Pat. Nos. 6,752,826 and 2003/0149471 A1, both of which are incorporated herein by reference.

Non-porous THORALON can be formed by mixing the polyetherurethane urea (BPS-215) and the surface modifying additive (SMA-300) in a solvent, such as dimethyl formamide (DMF), tetrahydrofuran (THF), dimethylacetamide (DMAC), dimethyl sulfoxide (DMSO). The composition can contain from about 5 wt % to about 40 wt % polymer, and different levels of polymer within the range can be used to fine tune the viscosity needed for a given process. The composition can contain less than 5 wt % polymer for some spray application embodiments. In one example, the composition can be dried to remove the solvent.

A variety of other biocompatible polyurethanes/polycarbamates and urea linkages (hereinafter "—C(O)N or CON type polymers") may also be employed. These include CON type polymers that preferably include a soft segment and a hard segment. The segments can be combined as copolymers or as blends. For example, CON type polymers with soft segments such as PTMO, polyethylene oxide, polypropylene oxide, polycarbonate, polyolefin, polysiloxane (i.e. polydimethylsiloxane), and other polyether soft segments made from higher homologous series of diols may be used. Mixtures of any of the soft segments may also be used. The soft segments also may have either alcohol end groups or amine end groups. The molecular weight of the soft segments may vary from about 500 to about 5,000 g/mole.

Preferably, the hard segment is formed from a diisocyanate and diamine. The diisocyanate may be represented by the formula OCN—R—NCO, where —R— may be aliphatic, aromatic, cycloaliphatic or a mixture of aliphatic and aromatic moieties. Examples of diisocyanates include MDI, tetramethylene diisocyanate, hexamethylene diisocyanate, trimethyhexamethylene diisocyanate, tetramethylxylylene diisocyanate, 4,4'-dicyclohexylmethane diisocyanate, dimer acid diisocyanate, isophorone diisocyanate, metaxylene diisocyanate, diethylbenzene diisocyanate, decamethylene 1,10 diisocyanate, cyclohexylene 1,2-diisocyanate, 2,4-toluene diisocyanate, 2,6-toluene diisocyanate, xylene diisocyanate, m-phenylene diisocyanate, hexahydrotolylene diisocyanate (and isomers), naphthylene-1,5-diisocyanate, 1-methoxyphenyl 2,4-diisocyanate, 4,4'-biphenylene diisocyanate, 3,3'-dimethoxy-4,4'-biphenyl diisocyanate and mixtures thereof.

The diamine used as a component of the hard segment includes aliphatic amines, aromatic amines and amines containing both aliphatic and aromatic moieties. For example, diamines include ethylene diamine, propane diamines, butanediamines, hexanediamines, pentane diamines, heptane diamines, octane diamines, m-xylylene diamine, 1,4-cyclohexane diamine, 2-methypentamethylene diamine, 4,4'-methylene dianiline, and mixtures thereof. The amines may also contain oxygen and/or halogen atoms in their structures.

Other applicable biocompatible polyurethanes include those using a polyol as a component of the hard segment. Polyols may be aliphatic, aromatic, cycloaliphatic or may contain a mixture of aliphatic and aromatic moieties. For example, the polyol may be ethylene glycol, diethylene glycol, triethylene glycol, 1,4-butanediol, 1,6-hexanediol, 1,8-octanediol, propylene glycols, 2,3-butylene glycol, dipropylene glycol, dibutylene glycol, glycerol, or mixtures thereof.

Biocompatible CON type polymers modified with cationic, anionic and aliphatic side chains may also be used. See, for example, U.S. Pat. No. 5,017,664.

Other biocompatible CON type polymers include: segmented polyurethanes, such as BIOSPAN; polycarbonate urethanes, such as BIONATE; and polyetherurethanes, such as ELASTHANE; (all available from POLYMER TECHNOLOGY GROUP, Berkeley, Calif.). Other biocompatible CON type polymers can include polyurethanes having siloxane segments, also referred to as a siloxane-polyurethane. Examples of polyurethanes containing siloxane segments include polyether siloxane-polyurethanes, polycarbonate siloxane-polyurethanes, and siloxane-polyurethane ureas. Specifically, examples of siloxane-polyurethane include polymers such as ELAST-EON 2 and ELAST-EON 3 (AORTECH BIOMATERIALS, Victoria, Australia); polytetramethyleneoxide (PTMO) and polydimethylsiloxane (PDMS) polyether-based aromatic siloxane-polyurethanes such as PURSIL-10, -20, and -40 TSPU; PTMO and PDMS polyether-based aliphatic siloxane-polyurethanes such as PURSIL AL-5 and AL-10 TSPU; aliphatic, hydroxy-terminated polycarbonate and PDMS polycarbonate-based siloxane-polyurethanes such as CARBOSIL-10, -20, and -40 TSPU (all available from POLYMER TECHNOLOGY GROUP). The PURSIL, PURSIL-AL, and CARBOSIL polymers are thermoplastic elastomer urethane copolymers containing siloxane in the soft segment, and the percent siloxane in the copolymer is referred to in the grade name. For example, PURSIL-10 contains 10% siloxane. These polymers are synthesized through a multi-step bulk synthesis in which PDMS is incorporated into the polymer soft segment with PTMO (PURSIL) or an aliphatic hydroxy-terminated polycarbonate (CARBOSIL). The hard segment consists of the reaction product of an aromatic diisocyanate, MDI, with a low molecular weight glycol chain extender. In the case of PURSIL-AL the hard segment is synthesized from an aliphatic diisocyanate. The polymer chains are then terminated with a siloxane or other surface modifying end group. Siloxane-polyurethanes typically have a relatively low glass transition temperature, which provides for polymeric materials having increased flexibility relative to many conventional materials. In addition, the siloxane-polyurethane can exhibit high hydrolytic and oxidative stability, including improved resistance to environmental stress cracking. Examples of siloxane-polyurethanes are disclosed in U.S. Pat. No. 6,655,931, which is incorporated herein by reference.

In addition, any of these biocompatible CON type polymers may be end-capped with surface active end groups, such as, for example, polydimethylsiloxane, fluoropolymers, polyolefin, polyethylene oxide, or other suitable groups. See, for example the surface active end groups disclosed in U.S. Pat. No. 5,589,563, which is incorporated herein by reference.

In other embodiments, the polymer coating may comprise a biocompatible polymer. A large number of biocompatible polymers are known in the art including bioabsorbable and nonbioabsorbable. The term "bioabsorbable" is used herein to refer to materials selected to dissipate upon implantation within a body, independent of which mechanisms by which dissipation can occur, such as dissolution, degradation, absorption and excretion. Recitation of a "non-bioabsorbable" or "biostable" material herein refers to a material, such as a polymer or copolymer, which remains in the body without substantial bioabsorption after a desired period of implantation, which can be a period of multiple years.

Any suitable non-bioabsorbable polymers may be used in the present invention. Examples of non-bioabsorbable polymers include polyurethanes, silicones, and polyanhydrides and other polymers such as polyolefins, polyisobutylene and ethylene-alphaolefin copolymers; phosphatidylcholine and phosphoryl choline polymers; xylylenes and derivatives such as parylene; polyhalo-olefins such as vinyl halide polymers and copolymers, polyvinyl halides including polyvinyl chloride, polytetrafluoroethylene, polyvinylidene halides including polyvinylidene fluoride and polyvinylidene chloride; polyacrylonitriles; polyvinyl ketones; polyvinyl ethers, such as polyvinyl methyl ether; polyvinyl aromatics, such as polystyrene; acrylic polymers and copolymers; polyvinyl esters, such as polyvinyl acetate; polymethacrylates such as poly(butylmethacrylate); polyvinyl amides such as polyvinyl pyrrolidone; copolymers of vinyl monomers with each other and olefins, such as ethylene-methyl methacrylate copolymers, acrylonitrile-styrene copolymers, isobutylene-styrene copolymers, acrylonitrile butadiene styrene resins, and ethylene-vinyl acetate copolymers; polyamides, such as poly (hexamethylene adipamide) and polycaprolactam; alkyd resins, polycarbonates; polyoxymethylenes; polyimides; polyethers; epoxy resins, polyurethanes; rayon; rayon-triacetate; cellulose acetate, cellulose butyrate; cellulose acetate butyrate; cellophane; cellulose nitrate; cellulose propionate; cellulose ethers; and carboxymethyl cellulose.

Biodegradable polymers may also be used in the present invention. Biodegradable polymers can be chosen to provide desired characteristics upon implantation at a desired point of treatment, such as a desired time for absorption. For example, a biodegradable material can be chosen to degrade or be absorbed within a body over a period of weeks or months. Certain biodegradable polymers are known to degrade within the body at differing rates based upon the polymer selected and the point of implantation. Suitable biodegradable polymers can be selected from any materials known in the art.

The following lists provide certain non-limiting illustrative examples of biodegradable materials that can be used in implantable medical devices. The listing of any biodegradable material having two or more chiral centers is understood to include compositions comprising each stereoisomer and compositions comprising any combination of stereoisomers. For example, recitation of "polylactic acid" (or "polylactide") in the lists below is understood to include poly-D,L-lactic acid, poly-L-lactic acid, and poly-D-lactic acid. The listing of biodegradable materials includes any co-polymers, mixtures and derivatives of two or more of the materials listed herein.

Accordingly, suitable biodegradable materials include: poly-alpha hydroxy acids (including polyactic acid or polylactide, polyglycolic acid, or polyglycolide), poly-beta hydroxy acids (such as polyhydroxybutyrate or polyhydroxyvalerate), epoxy polymers (including polyethylene oxide (PEO)), polyvinyl alcohols, polyesters, polyorthoesters, polyamidoesters, polyesteramides, polyphosphoesters, and polyphosphoester-urethanes. Examples of degradable polyesters include: a poly(hydroxyalkanoates), including poly (lactic acid) or (polylactide, PLA), poly(glycolic acid) or polyglycolide (PGA), poly(3-hydroxybutyrate), poly(4-hydroxybutyrate), poly(3-hydroxyvalerate), and poly(caprolactone), or poly(valerolactone). Examples of polyoxaesters include poly(alkylene oxalates) such as poly(ethylene oxalate)) and polyoxaesters containing amido groups. Other suitable biodegradable materials include: polyethers including polyglycols, ether-ester copolymers (copoly(ether-esters)) and polycarbonates. Examples of biodegradable polycarbonates include polyorthocarbonates, polyiminocarbonates, polyalykycarbonates such as poly(trimethylene carbonate), poly(1,3-dioxan-2-one), poly(p-dioxanone), poly(6,6-dimethyl-1,4-dioxan-2-one), poly(1,4-dioxepan-2-one), and poly(1,5-dioxepan-2-one). Suitable biodegradable materials can also include: polyanhydrides, polyimines (such as poly(ethylene imine) (PEI)), polyamides (including poly-N-(2-hydroxypropyl)-methacrylamide), poly(amino acids) (including a polylysine such as poly-L-lysine, or a polyglutamic acid such as poly-L-glutamic acid), polyphosphazenes (such as poly(phenoxy-co-carboxylatophenoxy phosphazene), polyorganophosphazines, polycyanoacrylates and polyalkylcyanoacrylates (including polybutylcyanoacrylate), polyisocyanates, and polyvinylpyrolidones. The biodegradable material can also be a modified polysaccharide, such as cellulose, chitin, dextran, starch, hydroxyethyl starch, polygluconate, hyaluronic acid, and elatin, as well as co-polymers and derivative thereof.

Naturally occurring polymers can also be used in or on the medical device, including: fibrin, fibrinogen, elastin, casein, collagens, chitosan, extracellular matrix (ECM), carrageenan, chondroitin, pectin, alginate, alginic acid, albumin, dextrin, dextrans, gelatins, mannitol, n-halamine, polysaccharides, poly-1,4-glucans, starch, hydroxyethyl starch (HES), dialdehyde starch, glycogen, amylase, hydroxyethyl amylase, amylopectin, glucoso-glycans, fatty acids (and esters thereof), hyaluronic acid, protamine, polyaspartic acid, polyglutamic acid, D-mannuronic acid, L-guluronic acid, zein and other prolamines, alginic acid, guar gum, and phosphorylcholine, as well as co-polymers and derivatives thereof.

Various cross linked polymer hydrogels can also be used in forming the medical device, such as portions of the frame or coating on the frame. The hydrogel can be formed, for example, using a base polymer selected from any suitable polymer, preferably poly(hydroxyalkyl (meth)acrylates), polyesters, poly(meth)acrylamides, poly(vinyl pyrollidone) and poly(vinyl alcohol). A cross-linking agent can be one or more of peroxides, sulfur, sulfur dichloride, metal oxides, selenium, tellurium, diamines, diisocyanates, alkyl phenyl disulfides, tetraalkyl thiuram disulfides, 4,4'-dithiomorpholine, p-quinine dioxime and tetrachloro-p-benzoquinone. Also, boronic acid-containing polymer can be incorporated in hydrogels, with optional photopolymerizable group, into degradable polymer, such as those listed above.

Preferably, a bioabsorbable, biocompatible polymer is approved for use by the U.S. Food and Drug Administration (FDA). These FDA-approved materials include polyglycolic acid (PGA), polylactic acid (PLA), Polyglactin 910 (comprising a 9:1 ratio of glycolide per lactide unit, and known also as VICRYL™), polyglyconate (comprising a 9:1 ratio of glycolide per trimethylene carbonate unit, and known also as MAXON™), and polydioxanone (PDS). In general, these materials biodegrade in vivo in a matter of months, although some more crystalline forms can biodegrade more slowly. Optionally, one or more of the biodegradable polymers can be cross-linked by any suitable method to form a hydrogel biodegradable material. Optionally the stent graft assembly can be coated with polysaccharides, for example as disclosed in published U.S. Patent Application No. 2004/0091605 to Bayer et al., published on May 13, 2004 and incorporated herein by reference in its entirety.

Support Frame

In some aspects of the present invention, the medical device comprises a support frame. The support frame can be, for example, formed from wire, cut from a sheet or a section of cannula, molded or fabricated from a polymer, biomaterial, or composite material, or a combination thereof. The pattern (i.e., configuration of struts and cells) of the outer frame, which is selected to provide radial expandability to the device is also not critical for an understanding of the invention.

Any suitable support frame can be used as the support frame in the medical device. The specific support frame chosen will depend on several considerations, including the size and configuration of the vessel and the size, the nature of the medical device, the vessel in which the medical device is being implanted, the axial length of the treatment site, the inner diameter of the body vessel, the delivery method for placing the support frame, and other factors. Those skilled in the art can determine an appropriate implantable frame based on these and other factors.

The support frame is preferably a substantially cylindrical implantable frame defining a central longitudinal lumen. The support frame preferably defines a substantially cylindrical or elliptical lumen providing a conduit for fluid flow. The support frame can be made from a plurality of interconnected or disconnected struts. Junctures between the struts can occur at or between the ends of the struts. The junctures can be mechanical crimps, welds, or solder points. The support frame can also be machined or etched from a metal cylinder.

The struts can be straight, curved, or angled. The spaces between the struts can form squares, circles, rectangles, diamonds, hexagons, or any other functional geometry. The strut can have a number of crowns (e.g., from about three to about ten, including about five to about seven). Any number of struts can be used, including the range from about three to about, more narrowly about seven. Disconnected struts can be held in place by the thromboresistant coating.

The materials used in the support frame, including the outer frame and the radial members can be selected from a well-known list of suitable metals and polymeric materials appropriate for the particular application, depending on necessary characteristics that are required (self-expansion, high radial force, collapsibility, etc.). Suitable metals or metal alloys include: stainless steels (e.g., 316, 316L or 304), nickel-titanium alloys including shape memory or superelastic types (e.g., nitinol or elastinite); inconel; noble metals including copper, silver, gold, platinum, paladium and iridium; refractory metals including molybdenum, tungsten, tantalum, titanium, rhenium, or niobium; stainless steels alloyed with noble and/or refractory metals; magnesium; amorphous metals; plastically deformable metals (e.g., tantalum); nickel-based alloys (e.g., including platinum, gold and/or tantalum alloys); iron-based alloys (e.g., including platinum, gold and/or tantalum alloys); cobalt-based alloys (e.g., including platinum, gold and/or tantalum alloys); cobalt-chrome alloys (e.g., elgiloy); cobalt-chromium-nickel alloys (e.g., phynox); alloys of cobalt, nickel, chromium and molybdenum (e.g., MP35N or MP20N); cobalt-chromium-vanadium alloys; cobalt-chromium-tungsten alloys; platinum-iridium alloys; platinum-tungsten alloys; magnesium alloys; titanium alloys (e.g., TiC, TiN); tantalum alloys (e.g., TaC, TaN); L605; magnetic ferrite; bioabsorbable materials, including magnesium; or other biocompatible metals and/or alloys thereof.

In various embodiments, the support frame comprises a metallic material selected from stainless steel, nickel, silver, platinum, gold, titanium, tantalum, iridium, tungsten, a self-expanding nickel-titanium alloy, Nitinol, or inconel.

One particularly preferred material for forming a frame is a self-expanding material such as the superelastic nickel-titanium alloy sold under the tradename Nitinol. Materials having superelastic properties generally have at least two phases: a martensitic phase, which has a relatively low tensile strength and which is stable at relatively low temperatures, and an austenitic phase, which has a relatively high tensile strength and which can be stable at temperatures higher than the martensitic phase. Shape memory alloys undergo a transition between an austenitic phase and a martensitic phase at certain temperatures. When they are deformed while in the martensitic phase, they retain this deformation as long as they remain in the same phase, but revert to their original configuration when they are heated to a transition temperature, at which time they transform to their austenitic phase. The temperatures at which these transitions occur are affected by the nature of the alloy and the condition of the material. Nickel-titanium-based alloys (NiTi), wherein the transition temperature is slightly lower than body temperature, are preferred for the present invention. It can be desirable to have the transition temperature set at just below body temperature to insure a rapid transition from the martinsitic state to the austenitic state when the frame can be implanted in a body lumen.

Preferably, the support frame comprises a self-expanding nickel titanium (NiTi) alloy material. The nickel titanium alloy sold under the tradename Nitinol is a suitable self-expanding material that can be deformed by collapsing the frame and creating stress which causes the NiTi to reversibly change to the martensitic phase. The support frame can be restrained in the deformed condition inside a delivery sheath typically to facilitate the insertion into a patient's body, with such deformation causing the isothermal phase transformation. Once within the body lumen, the restraint on the support frame can be removed, thereby reducing the stress thereon so that the superelastic support frame returns towards its original undeformed shape through isothermal transformation back to the austenitic phase. Other shape memory materials may also be utilized, such as, but not limited to, irradiated memory polymers such as autocrosslinkable high density polyethylene (HDPEX). Shape memory alloys are known in the art and are discussed in, for example, "Shape Memory Alloys," Scientific American, 281: 74-82 (November 1979), incorporated herein by reference.

Some embodiments provide support frames that are not self-expanding, or that do not comprise superelastic materials. For example, in other embodiments, the support frame can comprise silicon-carbide (SiC). For example, published U.S. Patent Application No. US2004/034409 to Hueblein et al., published on Feb. 14, 2004 and incorporated in its entirety herein by reference, discloses various suitable frame materials and configurations.

Other suitable materials used in the support frame include carbon or carbon fiber; cellulose acetate, cellulose nitrate, silicone, polyethylene teraphthalate, polyurethane, polyamide, polyester, polyorthoester, polyanhydride, polyether sulfone, polycarbonate, polypropylene, high molecular weight polyethylene, polytetrafluoroethylene, or another biocompatible polymeric material, or mixtures or copolymers of these; polylactic acid, polyglycolic acid or copolymers thereof, a polyanhydride, polycaprolactone, polyhydroxybutyrate valerate or another biodegradable polymer, or mixtures or copolymers of these; a protein, an extracellular matrix component, collagen, fibrin or another biologic agent; or a suitable mixture of any of these.

Graft Members

In some aspects of the present invention, the medical device comprises a graft member. The graft member is formed of a biocompatible graft material. Examples of biocompatible graft materials include polyesters, such as Dacron® (polyethylene terphthalate or PET); fluorinated polymers, such as PTFE (polytetrafluoroethylene) and Teflon® (expanded polytetrafluoroethylene or ePTFE); polyurethanes such as THORALON™; polyamides such as nylon; or any other suitable material such as collagenous extracellular matrix (ECM) material including small intestine submucosa (SIS), which is commercially available from Cook Biotech, West Lafayette, Ind., U.S.A. Besides SIS, examples of ECM's include pericardium, stomach submucosa, liver basement membrane, urinary bladder submucosa, tissue mucosa, and dura mater.

Graft materials may include textiles in sheets or tubes containing a biocompatible polymer. Examples of biocompatible polymers from which sheets can be formed include polyesters, such as polyethylene terephthalate, polylactide, polyglycolide and copolymers thereof; fluorinated polymers, such as polytetrafluoroethylene (PTFE), expanded PTFE and poly(vinylidene fluoride); polysiloxanes, including polydimethyl siloxane; and polyurethanes, including polyetherurethanes, polyurethane ureas, polyetherurethane ureas, polyurethanes containing carbonate linkages and polyurethanes containing siloxane segments. In addition, materials that are not inherently biocompatible may be subjected to surface modifications in order to render the materials biocompatible. Examples of surface modifications include graft polymerization of biocompatible polymers from the material surface, coating of the surface with a crosslinked biocompatible polymer, chemical modification with biocompatible functional groups, and immobilization of a compatibilizing agent such as heparin or other substances. Thus, any polymer that may be formed into a sheet can be used to make a graft material, provided the final material is biocompatible. Polymers that can be formed into a sheet include polyolefins, polyacrylonitrile, nylons, polyaramids and polysulfones, in addition to polyesters, fluorinated polymers, polysiloxanes and polyurethanes as listed above. Preferably the graft is made of one or more polymers that do not require treatment or modification to be biocompatible.

Textile materials may be woven (including knitted) textiles or nonwoven textiles. Nonwoven textiles are fibrous webs that are held together through bonding of the individual fibers or filaments. The bonding can be accomplished through thermal or chemical treatments or through mechanically entangling the fibers or filaments. Because nonwovens are not subjected to weaving or knitting, the fibers can be used in a crude form without being converted into a yarn structure. Woven textiles are fibrous webs athat have been formed by knitting or weaving. The woven textile structure may be any kind of weave including, for example, a plain weave, a herringbone weave, a satin weave, or a basket weave. A textile material contains fibers and interstices between the fibers.

In one example of woven textiles, knitted textiles include weft knit and warp knit fiber arrays. Weft knit fabric structures (including double-knit structures) utilize interlocked fiber loops in a filling-wise, or weft, direction, while warp knit structures utilize fabric loops interlocked in a lengthwise, or warp direction. Weft knit structures generally are more elastic than warp knit structures, but the resiliency of warp kit fabrics is satisfactory to provide a substantial degree of elasticity, or resiliency, to the fabric structure without substantially relying on tensile fiber elongation for such elasticity. Weft knit fabrics generally have two dimensional elasticity (or stretch), while warp knit fabrics generally have unidirectional (width wise) elasticity. The different elasticity properties of the various knit or woven structures my be beneficially adapted to the functional requirement of the particular graft material application. In some cases, where little elasticity is desired, the fabric may be woven to minimize in plane elasticity by yet provide flexibility. For large diameter vascular grafts (6 mm diameter or larger) and various reconstructive fabric applications, polyethylene terephthalate fiber fabric arrays of suitably small fiber size may be utilized. Commercially available woven and knitted fabrics of medical grade Dacron fibers including, single and double velour graft fabrics, stretch Dacron graft fabric and Dacron mesh fabrics may be used in accordance with the present invention. For smaller vascular fraft applications (less than 6 mm diameter), and for other applications for which suitable substrates of desired structure are not commercially available, special manufacture may be necessary.

Woven fabrics may have any desirable shape, size, form and configuration. For example, the fibers of a woven fabric may be filled or unfilled. Examples of how the basic unfilled fibers may be manufactured and purchased are indicated in U.S. Pat. No. 3,772,137, by Tolliver. Fibers similar to those described are currently being manufactured by the DuPont Company from polyethylene terephthalate (often know as "DACRON™" when manufactured by DuPont), and by other companies from various substances.

Preferred textiles include those formed from polyethylene terephthalate and PTFE. These materials are inexpensive, easy to handle, have good physical characteristics and are suitable for clinical application.

Bioactive Agents

In some aspects of the present invention, the medical device comprises a bioactive agent. The bioactive agent may be coated inside or outside of the lumen of the medical device. For example, the bioactive agent may be coated on the luminal surface of the medical device. In other aspects the bioactive agent may be coated on the abluminal surface of the medical device. The bioactive agent may be incorporated in the polymer coating, coated on top of the polymer coating or between the polymer coating and medical device.

When the present invention comprises a bioactive agent, the bioactive agent is preferably a thromboresistant bioactive agent. The thromboresistant bioactive agent can be included in any suitable part of an implantable medical device. Selection of the type of thromboresistant bioactive, the portions of the medical device comprising the thromboresistant bioactive agent, and the manner of attaching the thromboresistant bioactive agent to the medical device can be chosen to perform a desired therapeutic function upon implantation. For example, a therapeutic bioactive agent can be combined with a biocompatible polyurethane, impregnated in an extracellular matrix material, incorporated in an implantable support frame or coated over any portion of the medical device. In one aspect, the medical device can comprise a thromboresistant bioactive agent coated on the surface of the medical device, preferably the luminal surface of the medical device.

Medical devices comprising an antithrombogenic bioactive agent are particularly preferred for implantation in areas of the body that contact blood. An antithrombogenic bioactive agent is any therapeutic agent that inhibits or prevents thrombus formation within a body vessel. The medical device can comprise any suitable antithrombogenic bioactive agent. Types of antithrombotic bioactive agents include anticoagulants, antiplatelets, and fibrinolytics. Anticoagulants are bioactive agents which act on any of the factors, cofactors, activated factors, or activated cofactors in the biochemical cascade and inhibit the synthesis of fibrin. Antiplatelet bioactive agents inhibit the adhesion, activation, and aggregation of platelets, which are key components of thrombi and play an important role in thrombosis. Fibrinolytic bioactive agents enhance the fibrinolytic cascade or otherwise aid in dissolution of a thrombus. Examples of antithrombotics include but are not limited to anticoagulants such as thrombin, Factor Xa, Factor VIIa and tissue factor inhibitors; antiplatelets such as glycoprotein IIb/IIIa, thromboxane A2, ADP-induced glycoprotein IIb/IIIa, and phosphodiesterase inhibitors; and fibrinolytics such as plasminogen activators, thrombin activatable fibrinolysis inhibitor (TAFI) inhibitors, and other enzymes which cleave fibrin.

Further examples of antithrombotic bioactive agents include anticoagulants such as heparin, low molecular weight heparin, covalent heparin, synthetic heparin salts, coumadin, bivalirudin (hirulog), hirudin, argatroban, ximelagatran, dabigatran, dabigatran etexilate, D-phenalanyl-L-poly-L-arginyl, chloromethyl ketone, dalteparin, enoxaparin, nadroparin, danaparoid, vapiprost, dextran, dipyridamole, omega-3 fatty acids, vitronectin receptor antagonists, DX-9065a, CI-1083, JTV-803, razaxaban, BAY 59-7939, and LY-51,7717; antiplatelets such as eftibatide, tirofiban, orbofiban, lotrafiban, abciximab, aspirin, ticlopidine, clopidogrel, cilostazol, dipyradimole, nitric oxide sources such as sodium nitroprussiate, nitroglycerin, S-nitroso and N-nitroso compounds; fibrinolytics such as alfimeprase, alteplase, anistreplase, reteplase, lanoteplase, monteplase, tenecteplase, urokinase, streptokinase, or phospholipid encapsulated microbubbles; and other bioactive agents such as endothelial progenitor cells or endothelial cells.

An antithrombogenic bioactive agents can be incorporated in or applied to portions of the stent graft assembly by any suitable method that permits adequate retention of the bioactive agent material and the effectiveness thereof for an intended purpose upon implantation in the body vessel. The configuration of the bioactive agent on or in the medical device will depend in part on the desired rate of elution for the bioactive. Bioactive agents can be coated directly on the medical device surface or can be adhered to a medical device surface by means of a coating. For example, a bioactive agent can be blended with a polymer and spray or dip coated on the device surface. A bioactive agent material can be posited on the surface of the medical device and a porous coating layer can be posited over the bioactive agent material according to the methods of the present invention. In this embodiment, the bioactive agent can diffuse through the porous coating layer. Multiple porous coating layers applied by the method of the present inventions and or pore size can be used to control the rate of diffusion of the bioactive agent material. In some aspects, a nonporous coating is desirable wherein the rate of diffusion of the bioactive agent material through the coating layer is controlled by the rate of dissolution of the bioactive agent material in the coating layer. Nonporous coatings can be applied to the medical device by the methods of the present invention.

The bioactive agent material can also be dispersed throughout the coating, by for example, blending the bioactive agent with the polymer solution that forms the coating. If the coating is biostable, the bioactive agent can diffuse through the coating layer. If the coating is biodegradable, the bioactive agent is released upon erosion of the biodegradable coating.

Bioactive agents may be bonded to the coating layer directly via a covalent bond or via a linker molecule which covalently links the bioactive agent and the coating layer. Alternatively, the bioactive agent may be bound to the coating layer by ionic interactions including cationic polymer coatings with anionic functionality on bioactive agent, or alternatively anionic polymer coatings with cationic functionality on the bioactive agent. Hydrophobic interactions may also be used to bind the bioactive agent to a hydrophobic portion of the coating layer. The bioactive agent may be modified to included a hydrophobic moiety such as a carbon based moiety, silicon-carbon based moiety or other such hydrophobic moiety. Alternatively, the hydrogen bonding interactions may be used to bind the bioactive agent to the coating layer.

Other examples of bioactive agents include: antiproliferative/antimitotic agents including natural products such as vinca alkaloids (i.e. vinblastine, vincristine, and vinorelbine), paclitaxel, epidipodophyllotoxins (i.e. etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagine); antiplatelet agents such as (GP) IIb/IIIa inhibitors and vitronectin receptor antagonists; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nirtosoureas (carmustine (BCNU) and analogs, streptozocin), trazenes-dacarbazinine (DTIC); antiproliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine {cladribine}); platinum coordination complexes (cisplatin, carboplatin), procarbazine, hydroxyurea, mitotane, aminoglutethimide; hormones (i.e. estrogen); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory; antisecretory (breveldin); anti-inflammatory: such as adrenocortical steroids (cortisol, cortisone, fludrocortisone, prednisone, prednisolone, 6α-methylprednisolone, triamcinolone, betamethasone, and dexamethasone), non-steroidal agents (salicylic acid derivatives i.e. aspirin; para-aminophenol derivatives i.e. acetaminophen; indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressives (cyclosporine, tacrolimus (FK-506), sirolimus (rapamycin), tacrolimus, everolimus, azathioprine, mycophenolate mofetil); angiogenic agents: vascular endothelial growth factor (VEGF), fibroblast growth factor (FGF); angiotensin receptor blockers; nitric oxide and nitric oxide donors; anti-sense oligionucleotides and combinations thereof; cell cycle inhibitors, mTOR inhibitors, and growth factor receptor signal transduction kinase inhibitors; retenoids; cyclin/CDK inhibitors; endothelial progenitor cells (EPC); angiopeptin; pimecrolimus; angiopeptin; HMG co-enzyme reductase inhibitors (statins); metalloproteinase inhibitors (batimastat) and protease inhibitors.

Methods of Coating

Methods for coating an implantable medical device are provided. The method comprises applying a coating to the luminal and or abluminal surface of the medical device. The coating preferably comprises a thromboresistant coating such as a biocompatible polyurethane urea sold under the tradename THORALON.

A method of applying a coating to a luminal surface of an implantable medical device, comprising the steps of providing the implantable medical device defining a lumen and having a longitudinal axis; rotating the medical device about the longitudinal axis; applying a polymer in liquid form to the luminal surface; and at least partially solidifying the polymer while rotating. The method may further comprise any of the steps of applying a bioactive material between luminal surface of the medical device and the polymer; or admixing the first bioactive material with the first polymer in liquid form; or applying a bioactive material to an inner surface defined by the polymer.

In another embodiment, a method of applying a coating to an abluminal surface of an implantable medical device is provided, comprising the steps of providing a cylindrical container having a longitudinal axis; placing the medical device defining a lumen inside a cylindrical container; placing a polymer in liquid form between an inner surface of the cylindrical container and the abluminal surface of the medical device; rotating the cylindrical container about the longitudinal axis; and at least partially solidifying the polymer while rotating. The method may further comprise any of the steps of applying a bioactive material between abluminal surface of the medical device and the polymer; or admixing the bioactive material with the polymer in liquid form; or applying a bioactive material to an outer surface defined by the polymer. In some aspects, the method also provides for coating the luminal surface of the medical device, comprising the steps of applying a polymer in liquid form to a luminal surface of the medical device; and at least partially solidifying the polymer while rotating. The abluminal and luminal surfaces of the implantable medical device may be coated with the same or different polymer in liquid forms.

In the method of applying a coating to the luminal and or abluminal surface of a medical device, a lumen is provided. The lumen may be defined by any tubular object including, for example, a tube, a stent, a graft, a stent graft, a ring or plurality or combination thereof. The implantable medical device defining a lumen has a longitudinal axis coaxial with the lumen. The implantable medical device is rotated about its longitudinal axis by any suitable means, including a bed of rollers. In one aspect the rotation means is a hot dog roller such as the Lil' Diggity Hot Dog Roller or Hot Diggity Hot Dog Roller available from Gold Medal Products, Cincinnati, Ohio. The rollers are preferably made of stainless steel. The medical device is placed on the bed of rollers such that the longitudinal axis is parallel the axis of the rollers.

The implantable medical device may be placed directly on the rotation device, or it may be preferable to place the medical device within a tube or cylindrical container to facilitate rotation. The tube or cylindrical container may also protect the medical device from contact with the rotation device. The tube or cylindrical container may be formed of any suitable material which is compatible with the medical device, and preferably compatible with the coating layer or polymer. Preferably the tube or cylinder is constructed of glass, stainless steel or Teflon. When a cylindrical container is employed, the method may further comprise separating the medical device form the cylindrical container.

The polymer in liquid form is applied to the luminal surface of the implantable medical device or between the inner surface of the cylindrical container and the abluminal surface of the medical device to form a polymer coating. The polymer coating is preferably substantially uniform in thickness. The polymer in liquid form may be applied by any suitable means including spraying, dropping, dipping or pouring. The polymer in liquid form preferably comprises a volatile solvent. Suitable solvents include dimethylformamide, dimethylacetamide, dimethylsulfoxide, tetrahydrofuran, methylene chloride, and chloroform. The polymer is at least partially solidified by evaporating the solvent or drying the polymer in liquid solution. The solvent may be evaporated by applying heat, reducing the atmospheric pressure or a combination thereof. Multiple coatings of the polymer may be applied by allowing the polymer in liquid for to at least partially solidify before applying an additional coating.

The polymer in liquid form preferably comprises a thromboresistant material such as THORALON material. A solution for forming non-porous THORALON can be made by mixing the polyetherurethane urea (BPS-215) and the surface modifying additive (SMA-300) in a solvent, such as dimethyl formamide (DMF), tetrahydrofuran (THF), dimethyacetamide (DMAC), or dimethyl sulfoxide (DMSO). The polymer is liquid form composition can contain from about 5 wt % to about 40 wt % polymer, and different levels of polymer within the range can be used to fine tune the viscosity needed for a given process. The polymer in liquid form composition can contain less than 5 wt % polymer for some spray application embodiments.

A solution for forming porous THORALON can be formed by mixing the polyetherurethane urea (BPS-215), the surface modifying additive (SMA-300) and a particulate substance in a solvent. The particulate may be any of a variety of different particulates or pore forming agents, including inorganic salts. Preferably the particulate is insoluble in the solvent. The solvent may include dimethyl formamide (DMF), tetrahydrofuran (THF), dimethyacetamide (DMAC), dimethyl sulfoxide (DMSO), or mixtures thereof. The composition can contain from about 5 wt % to about 40 wt % polymer, and different levels of polymer within the range can be used to fine tune the viscosity needed for a given process. The composition can contain less than 5 wt % polymer for some spray application embodiments. The particulates can be mixed into the composition. For example, the mixing can be performed with a spinning blade mixer for about an hour under ambient pressure and in a temperature range of about 18° C. to about 27° C. The composition can be dried to remove the solvent, and then the dried material can be soaked in distilled water to dissolve the particulates and leave pores in the material. In another example, the composition can be coagulated in a bath of distilled water. Since the polymer is insoluble in the water, it will rapidly solidify, trapping some or all of the particulates. The particulates can then dissolve from the polymer, leaving pores in the material. It may be desirable to use warm water for the extraction, for example water at a temperature of about 60° C. The resulting pore diameter can also be substantially equal to the diameter of the salt grains.

Apparatus for Coating

Figure 3:
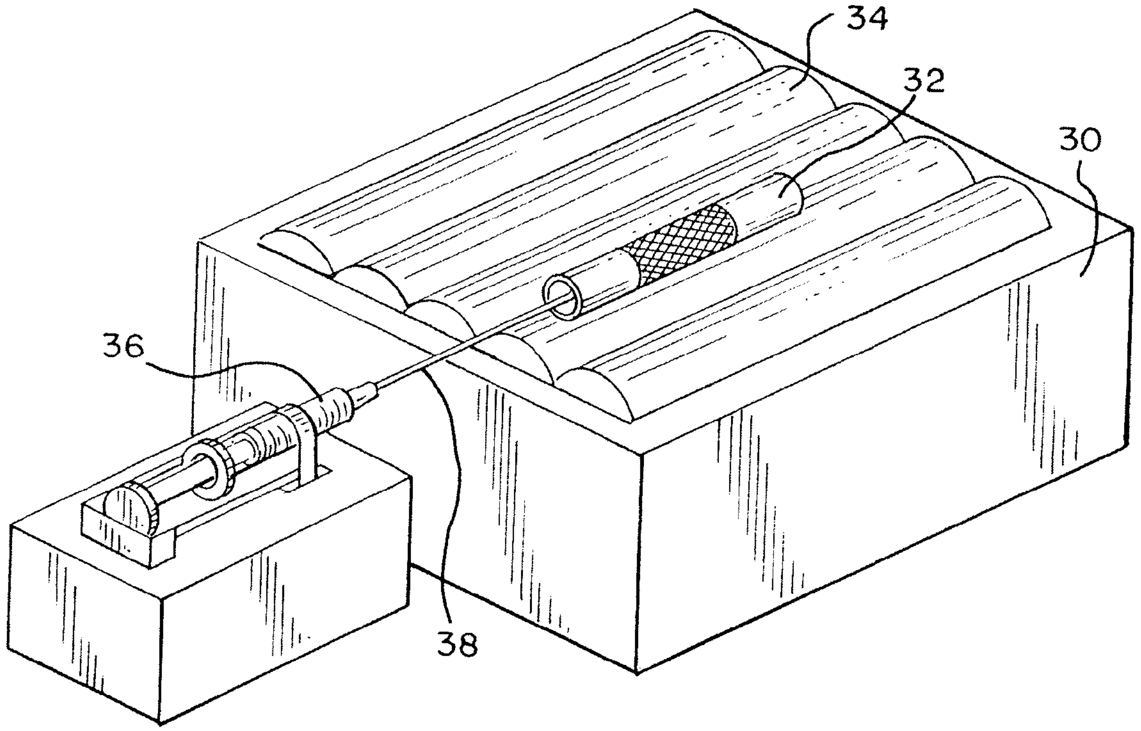
FIG. 3 is a perspective view of an apparatus for use in coating a medical device.

An apparatus for use in coating a medical device is provided. One illustrative apparatus is shown in FIG. 3. The apparatus comprises a lumen rotator 30 for rotating the lumen of the implantable medical device about its longitudinal axis. The lumen rotator comprises rollers 34 upon which the cylindrical container 32 is placed. A source of polymer in liquid form 36 is provided which is applied by an applicator 38 to the inside of the cylindrical container. The lumen rotator may comprise a heater. The heater may heat the rollers and thereby heat the implantable medical device. In other aspects, the apparatus may comprise a dryer. For example, the lumen rotator may be contained in a dryer, a fume hood, oven, or other vacuum chamber which assists in removal of volatile material from the polymer in liquid form.

Methods of Implantation

The implantable medical device as described herein can be delivered to any suitable body vessel, including a vein, artery, biliary duct, ureteral vessel, body passage or portion of the alimentary canal. Methods for delivering a medical device as described herein to any suitable body vessel are also provided, such as a vein, artery, biliary duct, ureteral vessel, body passage or portion of the alimentary canal. While many preferred embodiments discussed herein discuss implantation of a medical device in a vein, other embodiments provide for implantation within other body vessels. In another matter of terminology there are many types of body canals, blood vessels, ducts, tubes and other body passages, and the term "vessel" is meant to include all such passages.

In some embodiments, medical device of the present invention having a compressed delivery configuration with a very low profile, small collapsed diameter and great flexibility, may be able to navigate small or tortuous paths through a variety of body vessels. A low-profile medical device may also be useful in coronary arteries, carotid arteries, vascular aneurysms, and peripheral arteries and veins (e.g., renal, iliac, femoral, popliteal, sublavian, aorta, intercranial, etc.). Other nonvascular applications include gastrointestinal, duodenum, biliary ducts, esophagus, urethra, reproductive tracts, trachea, and respiratory (e.g., bronchial) ducts. These applications may optionally include a sheath covering the medical device. In one aspect, the medical device described herein are implanted from a portion of a catheter inserted in a body vessel.

Still other embodiments provide methods of treating a subject, which can be animal or human, comprising the step of implanting one or more medical devices as described herein. In some embodiments, methods of treating may also include the step of delivering a medical device to a point of treatment in a body vessel, or deploying a medical device at the point of treatment. Methods for treating certain conditions are also provided, such as, esophageal reflux, restenosis or atherosclerosis.

EXAMPLES

Example 1

This example illustrates coating the luminal surface of a medical device. An implantable medical device defining a lumen is placed on a Lil' Diggity Hot Dog Roller (Gold Medal Products, Cincinnati, Ohio). The longitudinal axis of the medical device is aligned with the rollers such that the medical device can rotate about the longitudinal axis.

A 40 wt % THORALON solution in dimethylacetamide (DMAC) is *prepared* by mixing the polyetherurethane urea (BPS-215) and the surface modifying additive (SMA-300) in DMAC. While the medical device is rotating about its longitudinal axis at 70° C., the luminal surface of the medical device is sprayed with the THORALON. The solvent is evaporated, and the THORALON is cured for 120 minutes to form to form the coated implantable medical device.

Example 2

This example illustrates coating the abluminal surface of a medical device. A glass tube is placed on a Lil' Diggity Hot Dog Roller (Gold Medal Products, Cincinnati, Ohio). The longitudinal axis of the glass tube is aligned with the rollers such that the glass tube can rotate about the longitudinal axis.

A 40 wt % THORALON solution in dimethylacetamide (DMAC) is prepared by mixing the polyetherurethane urea (BPS-215) and the surface modifying additive (SMA-300) in DMAC. While the glass tube is rotating about its longitudinal axis at 70° C., the luminal surface of the glass tube is sprayed with the THORALON solution. An implantable medical device in an unexpanded state is inserted into the lumen of the coated glass tube. The medical device is expanded such that the medical device is in contact with the THORALON coating. The solvent is evaporated from the THORALON solution, and the THORALON is cured.

After the THORALON is cured, the medical device is separated from the glass tube. In some cases, it may be helpful to insert a liquid between the glass tube and the THORALON coating to aid in separating the medical device from the glass tube. For example, the liquid may be an aqueous solution or an aqueous soap solution. The medical device is rinsed with water and dried to afford the coated implantable medical device.

Example 3

This example illustrates coating the luminal and abluminal surfaces of a medical device. A glass tube is placed on a Lil' Diggity Hot Dog Roller (Gold Medal Products, Cincinnati, Ohio). The longitudinal axis of the glass tube is aligned with the rollers such that the glass tube can rotate about the longitudinal axis.

A 40 wt % THORALON solution in dimethylacetamide (DMAC) is prepared by mixing the polyetherurethane urea (BPS-215) and the surface modifying additive (SMA-300) in DMAC. While the glass tube is rotating about its longitudinal axis at 70° C., the luminal surface of the glass tube is sprayed with the THORALON solution. An implantable medical device in an unexpanded state is inserted into the lumen of the coated glass tube. The medical device is expanded such that the medical device is in contact with the THORALON coating. The solvent is partially evaporated from the THORALON solution.

While the medical device is rotating about its longitudinal axis at 70° C., the luminal surface of the medical device is sprayed with the 40 wt % THORALON solution. The solvent is evaporated, and the THORALON is cured.

After the THORALON is cured, the medical device is separated from the glass tube. In some cases, it may be helpful to insert a liquid between the glass tube and the THORALON coating to aid in separating the medical device from the glass tube. For example, the liquid may be an aqueous solution or an aqueous soap solution. The medical device is rinsed with water and dried to afford the coated implantable medical device.

It is therefore intended that the foregoing detailed description be regarded as illustrative rather than limiting, and that it be understood that it is the following claims, including all equivalents, that are intended to define the spirit and scope of this invention.

I claim:

1. A method of forming a coating on an abluminal surface of an implantable medical device, comprising the steps of:
- providing a cylindrical container having a longitudinal axis and an inner surface;
- placing the medical device comprising a lumen inside and co-axially aligned with the cylindrical container;
- rotating the cylindrical container about the longitudinal axis, the cylindrical container positioned such that the longitudinal axis is horizontal;
- applying a first polymer in liquid form inside the cylindrical container;
- at least partially solidifying the first polymer while rotating: and
- expanding the medical device such that the abluminal surface of the medical device contacts the inner surface of the cylindrical container.

2. The method of claim 1, further comprising applying the first polymer in liquid form to the lumen of the medical device to thereby form a coating on the lumen.

3. The method of claim 2, further comprising:
- applying a second polymer in liquid form on the luminal surface of the cylindrical container;
- at least partially solidifying the second polymer while rotating to form an abluminal coating layer; and
- inserting the medical device inside the cylindrical container, wherein an abluminal surface of the medical device is in contact with the abluminal coating layer.

4. The method of claim 1, further comprising
- applying the first polymer in liquid form on the luminal surface of the cylindrical container, wherein partially solidifying the first polymer while rotating forms an abluminal coating layer; and
- inserting the medical device inside the cylindrical container, wherein an abluminal surface of the medical device is in contact with the abluminal coating layer.

5. The method of claim 2, wherein the first polymer comprises a polyurethane urea.

6. The method of claim 2, wherein the first polymer comprises a polyetherurethane urea blended with a siloxane containing surface modifying additive.

7. The method of claim 2, wherein the first polymer comprises a base polymer and about 0.5% to about 5% by weight of a surface modifying additive based on the weight of the base polymer;

where the surface modifying additive comprises polydimethylsiloxane and the reaction product of diphenylmethane diisocyanate and 1,4-butanediol; and where the base polymer is a polyetherurethane urea comprising polytetramethylene oxide and the reaction product of 4,4'-diphenylmethane diisocyanate and ethylene diamine.

8. The method of claim 3, wherein the second polymer comprises a polyurethane urea.

9. The method of claim 3, wherein the second polymer comprises a polyetherurethane urea blended with a siloxane containing surface modifying additive.

10. The method of claim 3, wherein the second polymer comprises a base polymer and about 0.5% to about 5% by weight of a surface modifying additive based on the weight of the base polymer;

where the surface modifying additive comprises polydimethylsiloxane and the reaction product of diphenylmethane diisocyanate and 1,4-butanediol; and where the base polymer is a polyetherurethane urea comprising polytetramethylene oxide and the reaction product of 4,4'-diphenylmethane diisocyanate and ethylene diamine.

11. The method of claim 1, wherein the medical device comprises a graft, stent, or ring.

12. The method of claim 1, further comprising applying a first bioactive agent to the medical device.

13. The method of claim 12, wherein the first bioactive agent is an antithrombogenic agent, antiplatelet agent, immunosuppressant agent, antiproliferative agent, fibrolytic agent, or antibacterial.

14. The method of claim 12, further comprising admixing the first bioactive agent with the first polymer in liquid form.

15. The method of claim 12, further comprising applying a first bioactive agent in contact with the polymer.

16. The method of claim 3, further comprising applying a second bioactive agent in contact with the second polymer.

17. The method of claim 4, further comprising applying a second bioactive agent in contact with the first polymer.

18. The method of claim 17, wherein the second bioactive agent is an antithrombogenic agent, antiplatelet agent, immunosuppressant agent, antiproliferative agent, fibrolytic agent, or antibacterial.

19. The method of claim 1, further comprising the steps placing the cylindrical container on a bed of rollers; and rotating the bed of rollers.

20. The method of claim 4, further comprising the separating the medical device comprising the abluminal coating layer from the cylindrical container.

* * * * *